(12) United States Patent
Kitani et al.

(10) Patent No.: US 7,614,426 B2
(45) Date of Patent: Nov. 10, 2009

(54) CAP FOR CONNECTOR

(75) Inventors: Ichiro Kitani, Fukuroi (JP); Katsuki Nagata, Fukuroi (JP); Shigeaki Funamura, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 178 days.

(21) Appl. No.: 12/018,764

(22) Filed: Jan. 23, 2008

(65) Prior Publication Data

US 2008/0195053 A1     Aug. 14, 2008

(30) Foreign Application Priority Data

Jan. 30, 2007    (JP) .............................. 2007-019791

(51) Int. Cl.
*F16L 55/10*    (2006.01)
(52) U.S. Cl. .................. 138/89; 138/96 R; 604/263; 215/306; 215/320; 215/355; 220/375
(58) Field of Classification Search .................. 138/89, 138/96 R; 604/263; 215/306, 320, 355; 220/375
See application file for complete search history.

(56) References Cited

U.S. PATENT DOCUMENTS

| | | | | |
|---|---|---|---|---|
| 4,636,313 A | * | 1/1987 | Vaillancourt | 210/436 |
| 4,935,010 A | * | 6/1990 | Cox et al. | 604/122 |
| 5,290,253 A | * | 3/1994 | Kira | 604/190 |
| 5,855,230 A | * | 1/1999 | Guala et al. | 138/89 |
| 2005/0203460 A1 | | 9/2005 | Kim | |
| 2007/0293822 A1 | * | 12/2007 | Crawford et al. | 604/175 |
| 2008/0103487 A1 | * | 5/2008 | Miyasaka | 604/537 |
| 2008/0200902 A1 | * | 8/2008 | Mabuchi | 604/537 |
| 2009/0177170 A1 | * | 7/2009 | Kitani et al. | 604/256 |

FOREIGN PATENT DOCUMENTS

| WO | 2004006981 A2 | 1/2004 |
|---|---|---|
| WO | 2006074935 A1 | 7/2006 |
| WO | 2007000066 A1 | 1/2007 |

OTHER PUBLICATIONS

Extended European Search Report issued in Application No. 08100331.1 dated May 29, 2008, 5 pages.

* cited by examiner

*Primary Examiner*—James F Hook

(57) ABSTRACT

A cap for a connector which can fill a male luer connector with only a fluid, such as a medicinal fluid, without leaving gas in the male luer connector. The cap for the connector comprises the cap body, the sliding part movable relative to the cap body, and the air filter placed at the tip end opening of the gas flow path forming part included in the sliding part. Also, the cap body comprises the cylindrical fitting part for liquid tightly fitting with the tip end opening of the male luer connector, and the cylindrical guide provided with the liquid outlet on its peripheral surface. Further, the liquid outlet can be opened or closed by shifting the gas flow path forming part within the cylindrical guide. Moreover, the cylindrical guide is placed within the recess portion to be guided between the gas flow path forming part and the containing wall.

4 Claims, 6 Drawing Sheets

CAP FOR CONNECTOR

FIELD OF THE INVENTION

The invention relates to a cap for a connector detachably attached to a male luer connector.

BACKGROUND OF THE INVENTION

Conventionally, a predetermined liquid medicine or blood and the like are supplied internally to the body of a patient by using a plurality of liquid transfusion tubes. In such a case, the tubes are communicated with each other by using connectors each attached to one end of each tube to connect each other. A male luer connector is attached to a tube upstream the flow of the liquid and a female luer connector attached to a tube downstream. The male luer connector is treated to remove gases such as air contained therein together with the upstream tube and only a liquid such as liquid medicine is filled in the connector before connecting to the female connector.

The liquid is flowed from the tube into the male luer connector while a cap including an air filter that does not allow to flow the liquid but gas is attached to the tip of the male luer connector, thereby removing only the gas contained in the liquid out by passing through the air filter (see, for example, Japanese Patent Unexamined Publication No. 2005-535379). The cap attached to the male luer connector comprises a lid attached to a generally cylindrical body, the lid having a pathway communicated with the body, a cylindrical absorbing member attached along the inner peripheral surface of the body, and an air filter provided within the pathway of the lid.

Therefore, when the liquid such as liquid medicine is supplied from the tube into the male luer connector with this cap attached thereto, if there is an air layer between the liquid, the liquid that firstly enter the cap is absorbed by the absorbing member and, then, the air is discharged to the exterior through the air filter. Thus, within the male luer connector, only the liquid not containing the air is filled therein.

However, since the amount of the liquid to be absorbed by the absorbing member is limited in the cap of the conventional male luer connector described above, when an amount of the liquid cannot be absorbed by the absorbing member before removing the air layer, the air that remained within the male luer connector raises a problem. Also, there is a problem that the operation for removing the air in such a case would be complicated.

In the light of the problems described above, the object of the invention is to provide a cap for a connector which can fill a male luer connector with only a liquid such as liquid medicine without any gases such as air remaining in the male luer connector.

SUMMARY OF THE INVENTION

In one aspect, the present invention is directed to a cap for a connector which is detachably attached to a male luer connector. The cap includes a cap body having a cylindrical fitting part fitted to seal the liquid with the male luer connector at the tip end opening portion thereof, and a cylindrical guide backwardly extended from the basal end of the cylindrical fitting part and provided with a liquid outlet at the peripheral surface thereof; and a sliding part movable in the axial direction of the cylindrical guide therein. The sliding part has a cylindrical gas flow path forming part for closing the liquid outlet when shifted to the cylindrical fitting part side and for opening the liquid outlet when shifted to the opposed side to the cylindrical fitting part side. An air filter which is provided within the gas flow path forming part allows passage of a gas but not the liquid from the pathway of the male luer connector to the gas flow path forming part by closing the tip end opening of the male luer connector when the gas flow path forming part is moved to the cylindrical fitting part side.

DESCRIPTION OF FIGURE NOTATIONS

10: male luer connector;
13: male luer part;
14: lock ring; 14*b*: internal thread;
20: cap for the connector;
21: cap body;
22: cylindrical fitting part; 22*b*: protruding streak;
23: cylindrical guide; 23*f*: liquid outlet;
24: outer peripheral wall;
25: sliding part;
27: gas flow path forming part;
28: containing wall;
29: operation part; and
30: air filter.

DETAILED DESCRIPTION OF THE INVENTION

Figure 1:
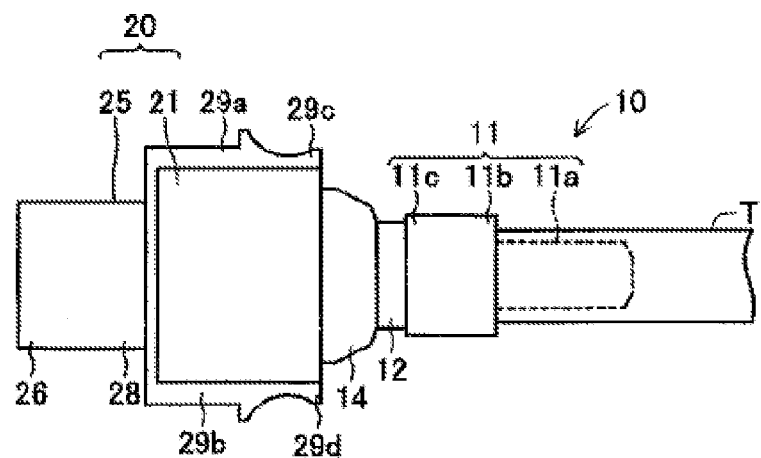
FIG. 1 is a side view illustrating one embodiment of the cap for the connector in accordance with the present invention, being connected to the male luer connector with the closed flow path.
Figure 2:
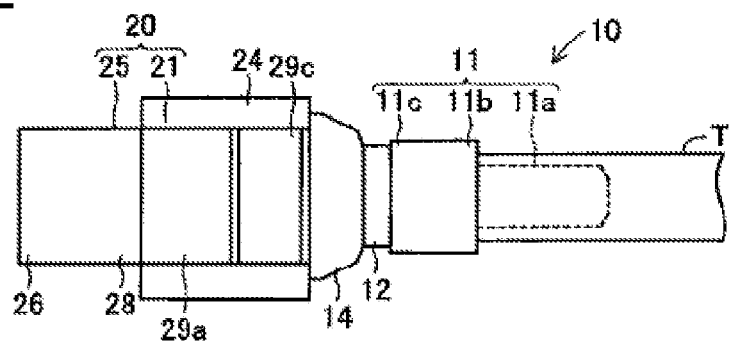
FIG. 2 is a top view illustrating the cap for the connector and the male luer connector of FIG. 1.
Figure 3:
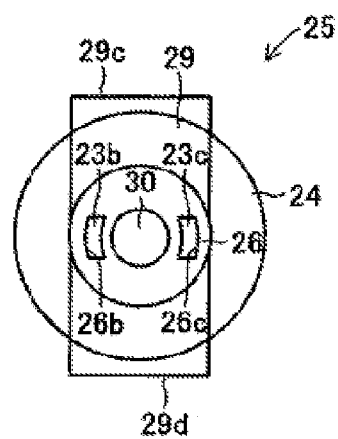
FIG. 3 is a front view illustrating the cap for the connector.
Figure 4:
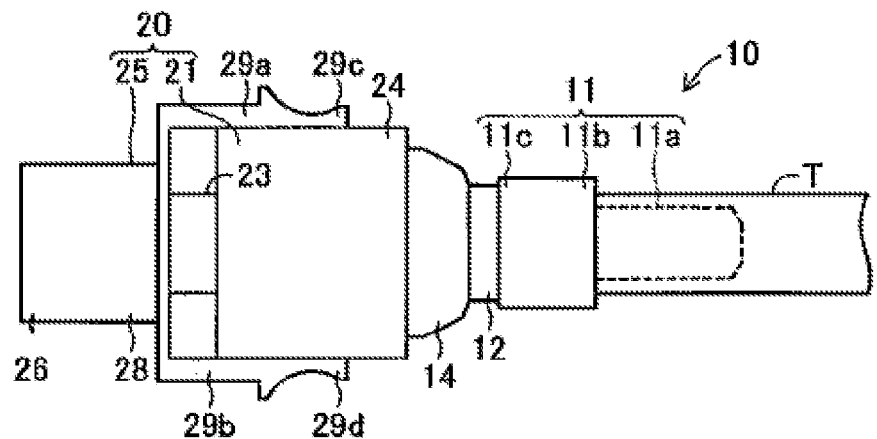
FIG. 4 is a side view illustrating the cap for the connector attached to the male luer connector with the flow path opened.
Figure 5:
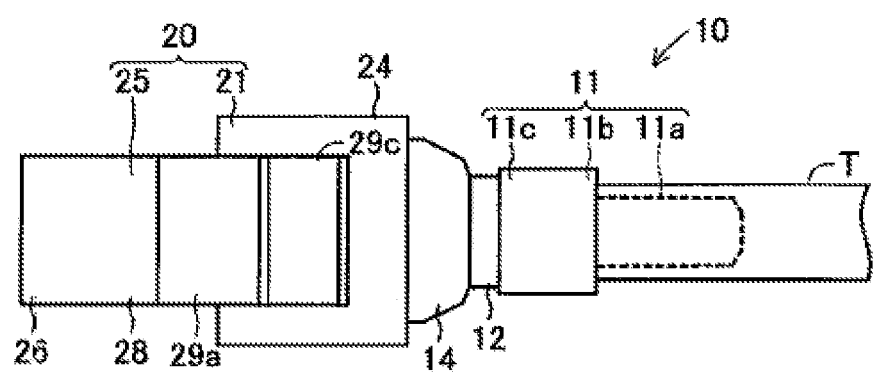
FIG. 5 is a top view illustrating the cap for the connector and the male luer connector of FIG. 4.

One embodiment of the cap for the connector in accordance with the invention will now be explained in detail with reference to the accompanied drawing in below. FIGS. 1 to 5 show a cap for a connector 20 of an embodiment in accordance with the invention which is attached to a male luer connector 10. This cap for the connector 20 is detachable to the male luer connector 10 and is capable of opening and closing a flow path formed therein as described in below. FIGS. 1 to 3 show the cap for the connector 20 in which the flow path is closed and FIGS. 4 and 5 show the cap for the connector 20 in which the flow path is opened.

The male luer connector 10 is connected to the tip end of a tube T and, as shown in FIGS. 6 to 9, comprises a basal part 11 at the posterior side, a connector body 12 comprising the central portion of the male luer connector, a male luer part 13 provided at the tip end side of the connector body 12, and a lock ring 14 extended from the outer peripheral surface to the tip end of the connector body 12. Also, the basal part 11, the connector body 12 and the male luer part 13 among these components comprising the male luer connector 10 are integrally formed by resin molding.

The basal part 11 is a portion which constructs a connecting portion to the tube T, comprising an inner barrel portion 11a to be inserted into the tube T, an outer barrel portion 11b for fixing the male luer connector 10 to the tip end of the tube T by covering the outer periphery of the tip end side of the tube T and pinching the tip end of the tube T with the inner barrel portion 11a, and an connection portion 11c for connecting the tip end of the inner barrel portion 11a with the tip end of the outer barrel portion 11b. That is, a recess portion opened at the rear end side thereof is formed between the inner barrel portion 11a and the outer barrel portion 11b, into which the tip end portion of the tube T can be inserted. Also, the tip end portion of the recess portion is occluded by the connection portion 11c. Further, the inner barrel 11a is formed such that its length is longer than that of the outer barrel lib and the connection portion 11c is formed into a ring shape which outer diameter is the same as that of the outer barrel portion 11b.

The connector body 12 is formed such that the outer diameter thereof is smaller than that of the outer barrel portion 11b and the connection portion 11c and the inner diameter is the same as that of the inner barrel portion 11a and the connection portion 11c, in which a recess portion 12a for sliding that provides the lightly smaller outer diameter than that of the tip end portion along the circumference is formed except for the tip end portion on the outer peripheral surface of the connector body 12. Further, the male luer part 13 is forwardly extended from the tip end portion of the connector body 12. The male luer part 13 is formed into a gradually tapered cylindrical shape from the basal portion side to the tip end side in which the outer diameter is reduced as close to the tip end portion and the inner diameter is the same as that of the basal portion 11 and the connector body 12. Moreover, the outer diameter of the basal portion of the male luer part 13 is almost the same as the outer diameter of the inner barrel portion 11a.

The lock ring 14 is formed into a generally cylindrical shape in which the basal portion 14a is narrower than the other portion thereof. Therefore, the lock ring 14 is rotatable relative to the connector body 12 about axis and movable in the axial direction of the connector body 12. An internal thread 14b is formed as a thread portion of the lock ring of the present invention is formed from the tip end portion to the central portion on the lock ring 14 in the axial direction thereof.

The cap for the connector 20 comprises a cap body 21 detachable relative to the male luer part 13 of the male luer connector 10, and a sliding part 25 mounted on the cap body 21 for slidably moving in the axial direction of the cap body 21. Also, the cap body 21 comprises a cylindrical fitting portion 22 forming the tip end portion of the cap body 21; a cylindrical guide 23 configuring the rear end portion of the cap body 21; and an outer peripheral wall 24 provided on the outer periphery of the cylindrical fitting portion 22.

In the explanation of the male luer connector 10 above, while the basal or rear end side is positioned in the right side and the tip or front end side is positioned in the left side in FIGS. 1 to 9 except for FIG. 3, in the cap for the connector 20 that will be explained hereinafter, the tip or front end side is positioned in the right side and the basal or rear end side is positioned in the left side. That is to say, the explanation is provided while one side where the male luer connector 10 and the cap for the connector 20 are opposed to each other is the tip or front end side and the other side is the basal or rear end side.

On the inner peripheral surface of the cylindrical fitting portion 22, a tapered surface 22a in which the diameter is gradually increased from the basal end to the tip end is formed, in which when the male luer part 13 is inserted into the tapered surface 22a, the outer peripheral surface of the male luer part 13 is liquid tightly contacted with the tapered surface 22a. Also, the axial length of the cylindrical fitting part 22 is slightly shorter than the axial length of the male luer part 13, whereby the tip end of the male luer part 13 is in the same position of the rear end of the cylindrical fitting part 22 as the outer peripheral surface of the male luer part 13 is liquid tightly contacted with the tapered surface 22a to place the tip end of the cylindrical fitting part 22 deviated from the front end surface of the connector body 12 with a slight distance maintained.

At the tip end of the outer peripheral surface of the cylindrical fitting part 22, a pair of protruding streaks 22b as a threaded portion of the cylindrical fitting part of the present invention is formed in the circumference direction of the cylindrical fitting part 22 with an interval between them. These protruding streaks 22b can be helically engaged with the internal thread 14b of the lock ring 14, thereby positioning the lock ring 14 on the outer periphery of the cylindrical fitting part 22 as the male luer part 13 is inserted in the cylindrical fitting part 22. Therefore, as the lock ring 14 is rotated in one direction about the axis while the male luer part 13 is inserted into the cylindrical fitting part 22 to contact the tip end of the internal thread 14b to the protruding streaks 22b, the cylindrical fitting part 22 is retained by engaging with the male luer part 13 by the helical fitting between the internal thread 14b and the protruding streaks 22b.

The cylindrical guide 23 is backwardly extended from the rear end of the cylindrical fitting part 22 and comprises a cylinder portion 23a, guide pieces 23b, 23c comprised by a pair of curved plated pieces positioned at the rear end and an engagement piece 23d having a flange shape formed between the cylinder portion 23a and the guide pieces 23b, 23c. The cylinder portion 23a is configured by a generally cylindrical body in which the outer diameter thereof is the same as that of the cylindrical fitting part 22 and the inner diameter is slightly greater than that of the cylindrical fitting part 22. Therefore, a step portion 23e is formed between the inner peripheral surface of the cylinder portion 23a and the inner peripheral surface of the cylindrical fitting part 22, whereby the step portion 23e is positioned on almost the same surface of the tip end surface of the male luer part 13 as the outer peripheral surface of the male luer part 13 is liquid tightly contacted with the tapered surface 22a of the cylindrical fitting part 22.

Figure 7:
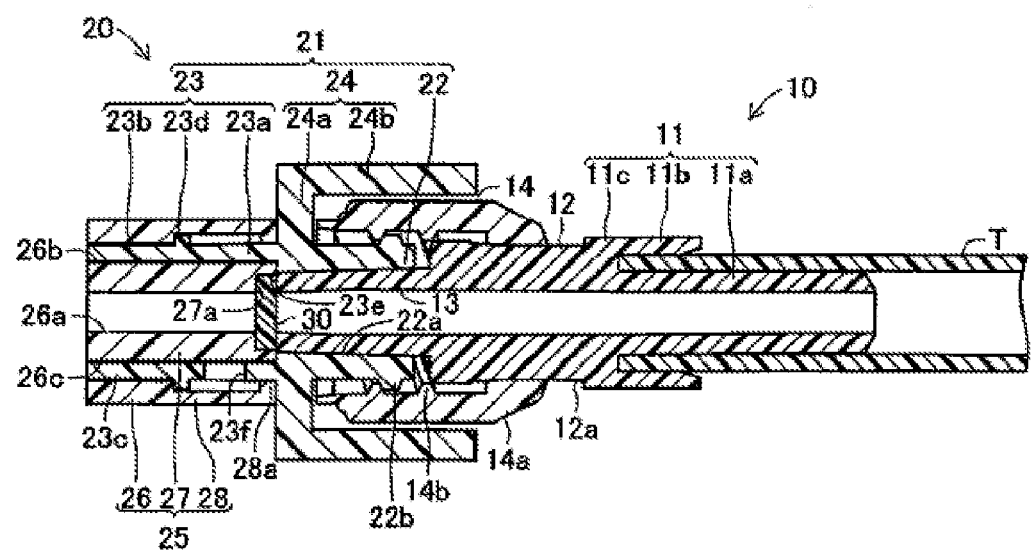
FIG. 7 is a cross sectional view of FIG. 2.
Figure 8:
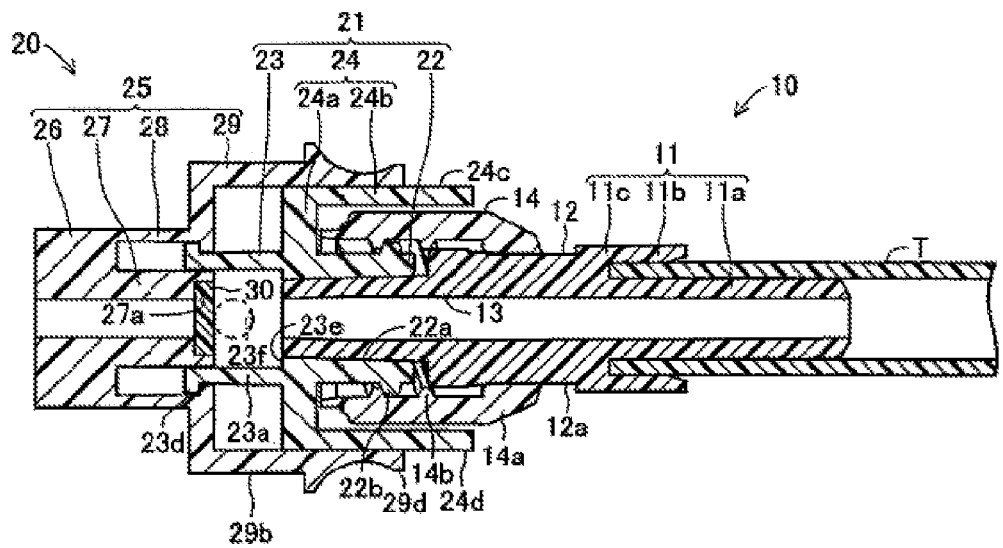
FIG. 8 is a cross sectional view of FIG. 4.

Furthermore, at one side op the periphery of the cylinder portion 23a, as shown in FIGS. 7 and 8, a circular liquid outlet 23f is formed so as to penetrate from the inside to the outside of the cylinder portion 23a. Each of the pair of guide pieces 23b and 23c comprise pieces, each having an arc shaped cross section, backwardly extended from the rear end of the cylinder portion 23a and placed as opposed to each other so as to form the angle of 180 degrees along the circumference of the cylindrical guide 23. The axial length of each of these guide pieces 23b and 23c is almost the same as that of the cylinder portion 23a. Further, in the boundary of the cylinder portion 23a and guide pieces 23b and 23c on the outer peripheral surface thereof, the flange like engagement piece 23d protruding toward the outer periphery is formed along the circumference.

Also, the outer peripheral wall 24 is comprised by a flange like connection portion 24a outwardly extended from the rear end on the outer peripheral surface of the cylindrical fitting part 22, and a cylindrical outer wall portion 24b forwardly extended from the outer periphery of the connection portion 24a. The outer wall portion 24b is formed so as to cover the outer peripheral surface of the lock ring 14 and plane portions 24c and 24d for guiding are formed on the upper and the lower surface of the outer peripheral surface thereof, respectively. Therefore, the upper and the lower portions are thinner than the other portions of the outer wall portion 24b.

Figure 10:
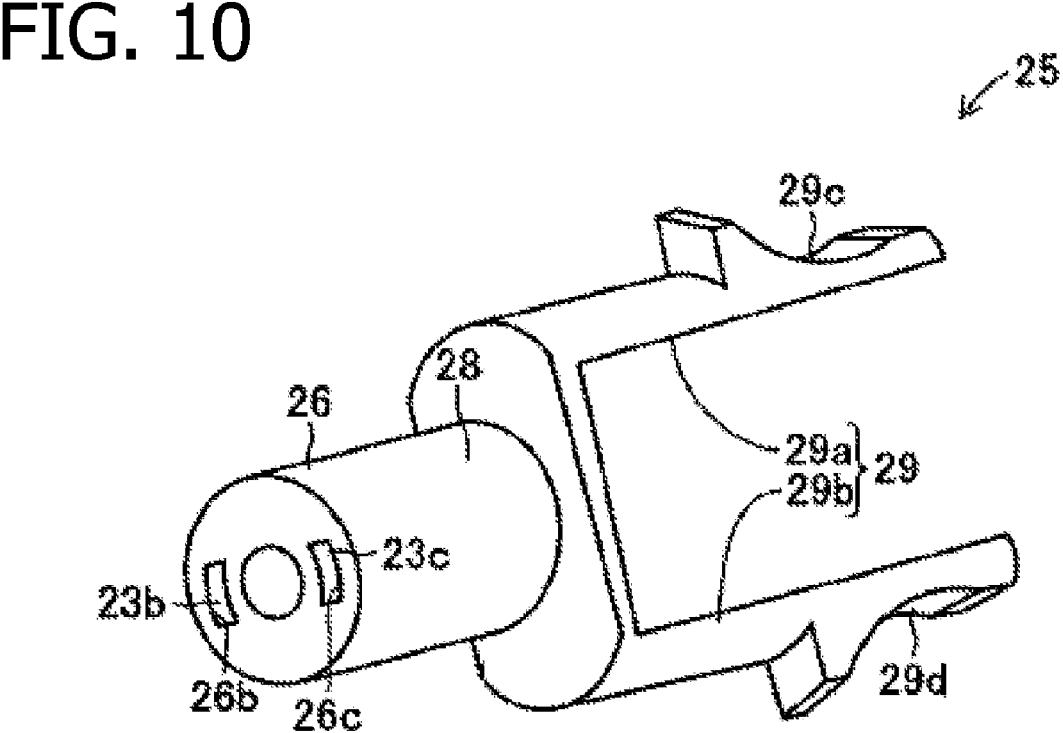
FIG. 10 is a perspective view of the sliding part.
Figure 11:
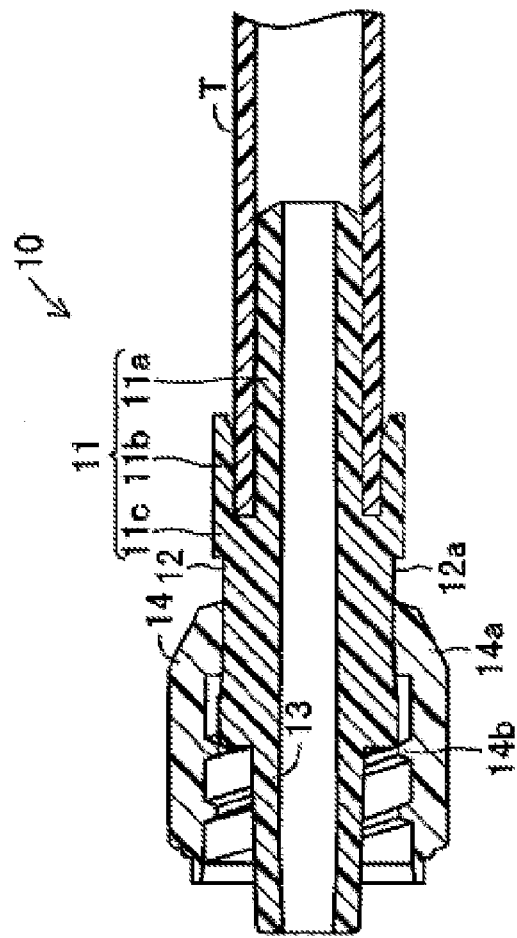
FIG. 11 is a cross sectional view of the cap for the connector exploded from the male luer connector.
Figure 11:
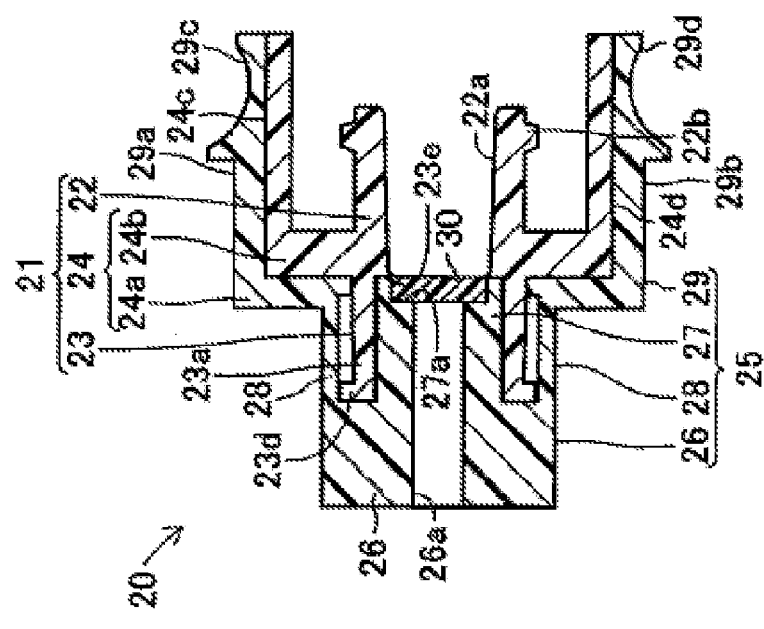

The sliding part 25 is formed in the configuration as shown in FIG. 10, comprising a generally cylindrical sliding basal end portion 26 positioned at the rear end; a gas flow path forming part 27 forwardly extended from the front inner peripheral of the sliding basal end portion 26; a containing wall 28 forwardly extended from the front outer periphery of the sliding basal end portion 26 and positioned at the outer periphery of the gas flow path forming part 27; and an operation portion 29 forwardly extended from the front end of the containing wall 28. The sliding basal end portion 26 is formed in a generally cylindrical shape having a thick wall and the short length in the axial direction thereof and including a gas flow path 26a formed therein for passing a gas along the central axis, in which holes to be guided 26b and 26c for receiving the guide pieces 23b and 23c to be movable of the cylindrical guide portion spaced from the gas flow path 26a.

Figure 6:
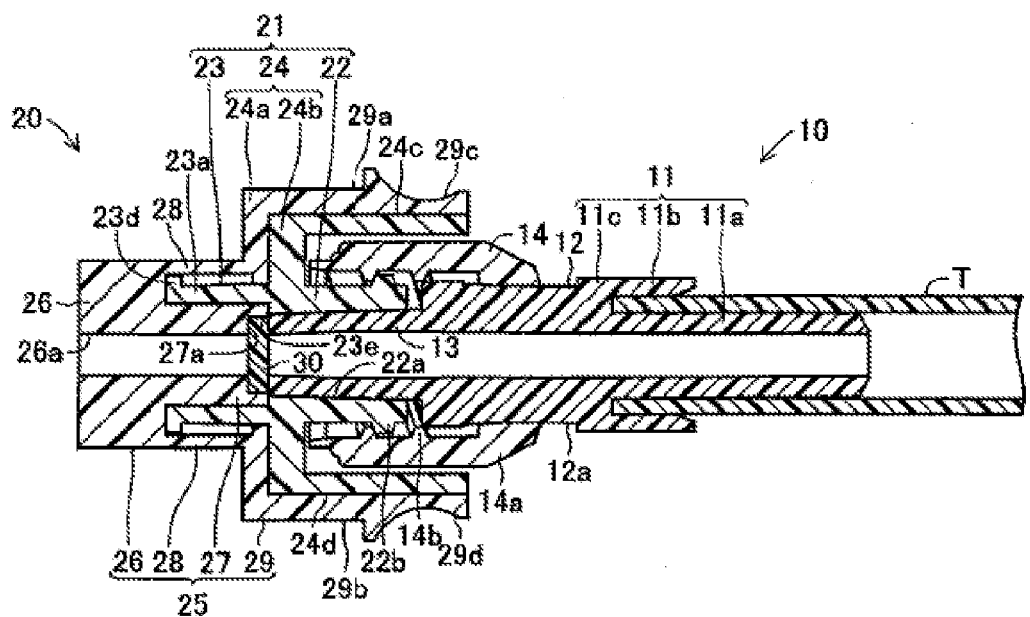
FIG. 6 is a cross sectional view of FIG. 1.
Figure 9:
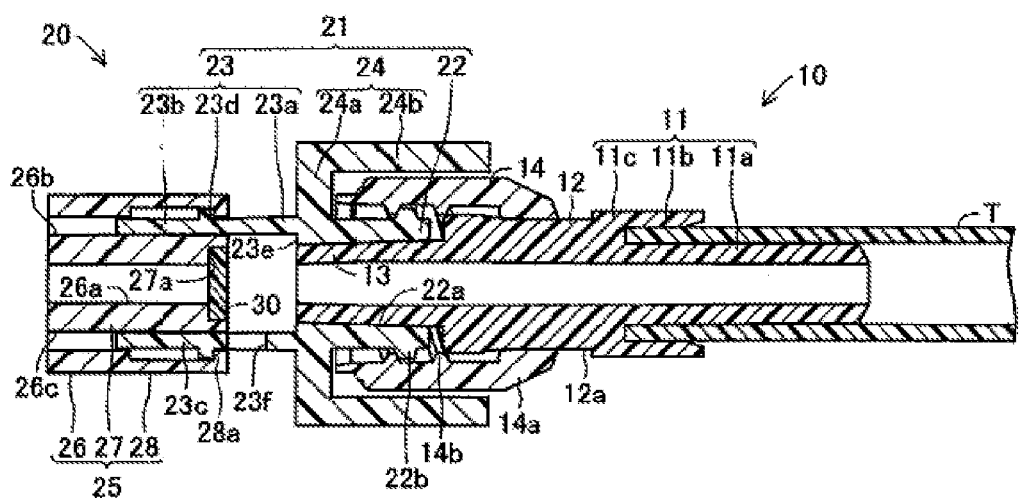
FIG. 9 is a cross sectional view of FIG. 5.

The gas flow path forming part 27 comprises a cylindrical body forwardly extended from the front end inner periphery of the sliding basal end portion 26, in which the inner diameter of the gas flow path forming part 27 is the same as that of the sliding basal end portion 26 and the outer diameter is the same as or slightly smaller than the inner diameter of the cylinder 23a of the cylindrical guide portion 23 to slidably move within the cylinder portion 23. In this case, as shown in FIGS. 6 and 7, when the gas flow path forming part 27 is forwardly moved to enter the cylinder portion 23a, the liquid outlet 23f is occluded and as shown in FIGS. 8 and 9, when the gas flow path forming part 27 is backwardly moved to out of the cylinder portion 23a, the liquid outlet 23f is opened. The inner of the gas flow path forming part 27 is communicated with the gas flow path 26a of the sliding basal end portion 26 to form a gas flow path together with the gas flow path 26a.

Then, at the tip end of the inner peripheral surface of the gas flow path forming part 27, a concaved step portion 27a is formed to which an air filter 30 is attached. This air filter 30 is characterized by that through which a liquid can not be past but a gas can. The containing wall 28 is comprised of a cylinder body forwardly extended from the front end outer periphery of the sliding basal end portion 26, in which the outer diameter there is the same as that of the sliding basal end portion 26 and the inner diameter is the same as or slightly greater than the outer diameter of the engagement piece 23d of the cylindrical guide 23. Furthermore, at the tip end of the inner peripheral surface of the containing wall 28, a ring shaped leaving out preventer 28a is formed along the circumference thereof, in which the inner diameter thereof is the same as or slightly greater than the outer diameter of the cylinder 23a.

Therefore, the containing wall 28 can be forwardly and backwardly moved together with the gas flow path forming part 27 relative to the cylinder 23a while the cylinder portion 23a is prevented from being out thereof by the cylinder 23a is positioned in the gap between the gas flow path forming part 27 and the containing wall 28 to engage the engagement piece 23a with the leaving out preventer 28a. The recess portion to be guided of the invention is formed in the gas between the containing wall 28 and the gas flow path forming part 27. Also, the operation portion 29 is comprised of a L shaped operation piece 29a upwardly extended from the upper of the tip end of the outer peripheral surface of the containing wall 28 and, then, angled to forwardly extend, and a L shaped operation piece 29b downwardly extended from the lower of the tip end of the outer peripheral surface of the containing wall 28 and, then, angled to forwardly extend.

Moreover, at the front end upper portion of the operation piece 29a, a finger receiver 29c is formed and a finger receiver 29d is formed at the front end lower portion of the operational piece 29b. The lower surface of the operation piece 29a and the upper surface of the operation piece 29b are formed to be planes, respectively, whereby the operation portion 29 is mounted on the outer peripheral surface of the outer wall portion 24b while the lower surface of the operation piece 29a is contacted with the plane 24c and the upper surface of the operation piece 29b is contacted with the plane 24d. The contact of the lower surface of the operation piece 29a and the plane 24c and the contact of the upper surface of the operation piece 29b and the plane 24d prohibit the rotation of the sliding part 25 about the axis, whereby the sliding part 25 is mounted to the cap body 21 in the condition where the sliding part 25 can be moved only the axial direction.

When the cap for the connector 20 is attached to the male luer connector 10 configured in this way, firstly, the male luer part 13 of the male luer connector 10 is inserted into the cylindrical fitting part 22 of the cap body 21. Secondary, the internal thread 14b is engaged with the protruding streak 22b by contacting the internal thread 14b of the lock ring 14 with the protruding streak 22b of the cylindrical fitting part 22 to provide a liquid tight coupling of the male luer connector 10 and the cylindrical fitting part 22 which is maintained. Therefore, as shown in FIGS. 6 and 7, the air filter 30 provided at the tip end of the gas flow path forming part 27 is contacted to the tip end of the male luer part 13 to occlude the tip end opening of the male luer part 13.

In this case, the engagement piece 23d of the cylindrical guide 23 is positioned at the deep end (the rear end) of the recess portion to be guided formed between the containing wall 28 and the gas flow path forming part 27, and the rear ends of guide pieces 23b and 23c are positioned at the rear ends of the holes to be guided 26b and 26c of the sliding basal end portion 26. Also, the liquid outlet 23f is occluded by the gas flow path forming part 27. In this condition, a liquid medicine is flowed from the basal end of the tube T to the male luer connector 10. Accordingly, the gas downstream the liquid medicine within the tube T is discharged to the exterior from the gas flow path within the sliding part 25 through the air filter 30 by the pressure of the liquid medicine, thereby providing the male luer connector 10 filled with the liquid medicine.

Alternatively, in the tube T, in case of a gas layer is in the upstream the liquid medicine reached to the male luer connector 10, the sliding part 25 is backwardly moved from the cap body 21 by operating the operation portion 29 with the finger receivers 29c and 29d held. Thus, as shown in FIGS. 8 and 9, the liquid outlet 28f is opened. In this case, the sliding part 25 is moved along the axis without rotating and the leaving out preventer 28a is contacted to the engagement piece 23d, thereby preventing the sliding part 25 from leaving out of the cap body 21.

Then, the liquid medicine positioned at the downstream of the gas is discharged from the liquid outlet 23f to the exterior together with gas, thereby providing the portion from the tube T to the male connector 10 filled by only the liquid medicine not containing the gas. The tube T and the male luer connector 10 are formed from a transparent resin material, whereby the discharge of the gas from the inside of the tube T or the male luer connector 10 can be visually checked. Therefore, the priming process is completed.

In this way, the male luer connector 10 after the completion of the priming process is connected to a female luer connector (not shown) connected to the tip end of a tube extended from a patient side to be supplied with the liquid medicine. Then, for example, when a set of liquid transfusion lines including an infusion cylinder, a roller clamp and the like is used, the downstream end of the tube connected to the female luer connector is connected to a puncturing member such as an indwelling needle for puncturing the needle and indwelling it in the body of the patient. Next, the liquid medicine is flowed from the infusion cylinder and the like into the tube T and the gas within the female connector or each tube and, then, the roller clam is adjusted to stop the flow of the liquid medicine. In this condition, the puncturing member is punctured at the predetermined site of the patient's body and the roller clamp is adjusted to adjust the flow rate of the liquid medicine flowing within the tubes to be proper. Accordingly, the liquid medicine can be supplied into the body of the patient from the infusion cylinder by the predetermined constant flow rate of the liquid medicine.

As described above, the cap for the connector 20 of the embodiment in accordance with the present invention includes the cap body 21 connected to the male luer connector 10 and the sliding part 25 movable relative to the cap body 21. Also, the cylindrical fitting part 22 being capable of liquid tightly fitting with the outer peripheral surface of the male luer connector 10 and the cylindrical guide 23 provided with the liquid outlet 23f on the peripheral surface thereof are provided to the cap body 21, whereby the liquid outlet 23f can be opened and closed by shifting the sliding part 25 while the gas flow path forming part 27 is placed within the cylindrical guide 23. And, the air filter 30 to the step portion 27a formed at the tip end of the gas flow path forming part 27.

Therefore, when the tip end opening of the male luer connector 10 is occluded by the air filter 30 by shifting the sliding part 25 to the side of the cap body 21, the liquid outlet 23f is occluded by the gas flow path forming part 27. In this condition, as the liquid medicine is flowed from the tube T to the male luer connector 10, the gas contained in the liquid medicine is discharged to the exterior through the air filter 30 and only the liquid medicine is remained within the male luer connector 10. Further, in case of the gas is remained with the tube T or the male luer connector 10 by being sandwiched between the liquid medicine, the sliding part 25 is backwardly moved from the cap body 21 to discharge the liquid medicine together with the gas positioned at the downstream side of the tube T or the male luer connector 10 to the exterior. Accordingly, the tube T or the male luer connector 10 can be in the condition where only the liquid medicine not containing the gas is filled therein.

In this case, since the sliding part 25 is forwardly moved relative to the cap body 21 while the cylindrical guide 23 is sandwiched between the gas flow path forming part 27 and the containing wall 28, the sliding part 25 is certainly and smoothly moved. Further, since the operation part 29 is provided to the sliding part 25, it can be avoided adhering the liquid medicine to a hand of an operator when the liquid medicine flowing from the male luer connector 10 as the sliding part 25 is backwardly moved from the cap body 21 is discharged from the liquid outlet 23f. Moreover, by providing the lock ring 14, the male luer connector 10 can firmly be connected with the cap for the connector 20 to be kept.

Furthermore, the cap for the connector in accordance with an embodiment of the invention is not intended to be limited to the embodiment described above and any modifications can be applied to the embodiment to carry out the invention. For example, while the cylindrical fitting part 22 is fitted over the male luer part 13 in the embodiment above, the cylindrical fitting part 22 may be formed to be narrower to internally fit with the male luer part 13. Alternatively, on both tip end surface of the cylindrical fitting part 22 and the male luer part 13, structures may be provided such that both surfaces can be fitted with each other, whereby the cylindrical fitting part 22 can be liquid tightly communicated with the male luer part 13.

Alternatively, while the threaded portion of the cylindrical fitting part 22 is comprised of the protruding streak 22b, the threaded part may be an external thread or a projection. Furthermore, while the male luer connector 10 includes the lock ring 14 in the embodiment described above, the lock ring may be omitted and the male luer part 13 may be fitted with the cylindrical fitting part 22 to fix to each other. Or, an elastic member activating such that the cap body 21 is closed to the sliding part 25 may be provided, in which the liquid outlet 23f can be opened by applying the force against the elasticity of the elastic member or, conversely, the liquid outlet 23f can be closed by releasing that force.

Moreover, while the male luer connector 10 is provided with a set of liquid transfusion lines including the infusion cylinder, the male luer connector may also be used to connect a blood transfusion line, other than the liquid transfusion lines, or another tube member for different purposes other. The configurations of the other portion of the cap for a connector in accordance with an embodiment of the invention may be changed within the technical scope of the invention.

The cap for the connector in accordance with an embodiment of the invention configured as described above includes the cap body connected to the male luer connector and the sliding part movable relative to the cap body. Also, the cap body is comprised by the cylindrical fitting part that can be fitted with and sealed for the liquid the male luer connector at the tip end opening side, and the cylindrical guide backwardly extended from the basal end of the cylindrical fitting part and provided with a liquid outlet at the peripheral surface thereof, whereby, the sliding part can close or open the liquid outlet by shifting within the cylindrical guide, the sliding guide comprising the cylindrical gas flow path forming part moving forwardly and backwardly relative to the tip end opening of the male luer connector. Further, at the tip end opening of the gas flow path forming part, the air filter that does not allow flow of the gas but the liquid is provided.

Therefore, when the tip end opening of the male luer connector is occluded by the air filter by shifting the gas flow path forming part to the cylindrical fitting part side, that is, the tip end opening of the male luer connector, the liquid outlet of the cylindrical guide is occluded by the gas flow path forming part. In this condition, when the liquid is flowed from the tube to the male luer connector, the gas such as air contained in the liquid as bubbles is passed through the air filter and only the liquid is remained in the male luer connector. Also, when the gas is not discharged to the exterior as sandwiched between the liquid, the gas flow path forming part is moved so as to remote from the tip end opening of the male luer connector by shifting backwardly the sliding part, thereby discharging the liquid together with the gas positioned at the tip end side of the male luer connector to the exterior.

Therefore, the male luer connector is in the state where it is filled with the liquid not containing the gas. In this case, the engagement of the luer connector at the end opening side and the cylindrical fitting part is configured such that whether the cylindrical fitting part may be comprised of a female luer to fit over the tip end opening side of the male luer connector, or the cylindrical fitting part is fitted within the male luer connector at the tip end opening portion. Further, the backward of the cylindrical guide extended from the basal end of the cylindrical fitting part is the direction in which the basal end is extended and it is deviated from the male luer connector. The cylindrical guide part is not limited to a cylindrical shape and may be in the shape of a triangular prism, a quadrangular prism or a prism having a cross section of any polygonal.

In another configuration of the cap for the connector in accordance with one embodiment of the invention, a cylindrical containing wall is provided with a distance from the gas flow path forming part at the outer periphery of the gas flow path forming part and a recess to be guided is formed between the gas flow path forming part and the cylindrical containing wall, in which the sliding part can be moved forwardly and backwardly relative to the cap body by positioning the cylindrical guide within the recess to be guided. By this configuration, the sliding part is forwardly and backwardly movable relative to the cap body while the cylindrical guide is sandwiched between the gas flow path forming part and the containing wall, whereby the sliding part can surely be imposed to the cap body as well as the movement of the sliding part can be smooth.

In yet another configuration of the cap for the connector in accordance with another embodiment of the invention, an operational part is provided to the sliding part, extending from the outer peripheral surface of the containing wall toward the outer peripheral surface of the cap body to allow its operation by hand when the sliding part is shifted relative to the cap body. By this configuration, the need for an operator to hold near the liquid outlet at the discharge of the liquid flowing from the male luer connector out of the liquid outlet of the cylindrical guide by shifting forwardly and backwardly the sliding part is eliminated, thereby preventing the liquid from adhering to the operator's hand.

In another configuration of the cap for the connector in accordance with an embodiment of the invention, the cylindrical fitting part can be fitted to seal the liquid with the outer peripheral surface at the tip end side of the male luer connector and a threaded portion is also provided on the outer peripheral surface of the cylindrical fitting part for engaging with a threaded part of a lock ring in which the threaded part is formed in the inner peripheral surface thereof to rotate the lock ring around the outer periphery of the male luer connector about axis, thereby helically connecting the threaded portion of the cylindrical fitting part to the male luer connector.

In this configuration, the tip end opening portion of the male luer connector is entered to the cylindrical fitting part and the inner peripheral surface of the cylindrical fitting part is helically connected with the outer peripheral surface of the tip end portion of the male luer connector while both surfaces are liquid tightly contacted, whereby the male luer connector and the cap for the connector can be firmly connected and maintained that condition. Alternatively, both threaded portions can be fitted with each other with the tip end opening of the male luer connector is slightly inserted into the cylindrical fitting part.

As the cylindrical fitting part enters the deeper side of the lock ring and the inner peripheral surface of the cylindrical fitting part is liquid tightly contacted to the outer peripheral surface of the male luer connector, the tip end of the gas flow path forming part is contacted with the tip end opening of the male luer connector. In this case, the treaded portions may be comprised of a combination of external and internal threads, or a combination of the internal thread and protrusion with groove which are engaged with the internal thread by rotating relative to the internal thread.

What is claimed is:

1. A cap for a connector detachably attached to a male luer connector, in which said cap for the connector comprises:
    a cap body including a cylindrical fitting part being capable of liquid tightly fitting with the tip end opening portion of said male luer connector and a cylindrical guide backwardly extended from the basal end of said cylindrical fitting part and provided with a liquid outlet on its peripheral surface;
    a sliding part having a cylindrical gas flow path forming part movable in the axial direction of said cylindrical guide within said cylindrical guide, in which said gas flow path forming part occludes said liquid outlet as moved toward said cylindrical fitting part and close said liquid outlet as moved toward the opposite side of said cylindrical fitting part; and
    an air filter provided to said gas flow path forming part, said air filter blocking the tip end opening of said male luer connector, said air filter passing through no liquid but a gas from a flow path of said male luer connector into said gas flow path forming part when said gas flow path forming part is moved toward said cylindrical fitting part.

2. The cap for the connector according to claim 1, further comprising a cylindrical containing wall at the outer periphery of said gas flow path forming part in said sliding part with a distance from said gas flow forming part to form a recess to be guided between said gas flow path forming part and said containing wall, in which said cylindrical guide is positioned within said recess to be guided, whereby said sliding part can be forwardly and backwardly moved relative to said cap body.

3. The cap for the connector according to claim 2, further comprising an operation part provided to said sliding part, said operation part being extended from the outer peripheral surface of said container wall to the outer peripheral surface of said cap body, said operation part being operational by holding in a hand when said sliding part is moved relative to said cap body.

4. The cap for the connector according to claim 1, wherein said cylindrical fitting part is liquid tightly fitted with the tip end outer peripheral surface of said male luer connector, further comprising a thread portion provided on the outer peripheral surface of said cylindrical fitting part and a lock ring in which a threaded portion is formed on the inner peripheral surface so as to be rotatable about the axis of said male luer connector on its peripheral surface, whereby said lock ring can be connected to said male luer connector by helically fitting said threaded portion of said lock ring with said threaded portion of said cylindrical fitting part.

* * * * *